United States Patent [19]
Hill et al.

[11] Patent Number: 5,637,757
[45] Date of Patent: Jun. 10, 1997

[54] ONE-POT SYNTHESIS OF RING-BROMINATED BENZOATE COMPOUNDS

[75] Inventors: John E. Hill; Nicolai A. Favstritsky; Rastko I. Mamuzic, all of West Lafayette, Ind.; Bhabatosh Bhattacharya, Lafayette, all of Ind.

[73] Assignee: Great Lakes Chemical Corporation, West Lafayette, Ind.

[21] Appl. No.: 420,125

[22] Filed: Apr. 11, 1995

[51] Int. Cl.$^6$ ................................................. C07C 69/76
[52] U.S. Cl. ................................................. 560/103
[58] Field of Search ................................. 560/103

[56] References Cited

U.S. PATENT DOCUMENTS

| | | |
|---|---|---|
| 5,049,697 | 9/1991 | Bohen et al. . |
| 5,208,366 | 5/1993 | Bohen et al. . |
| 5,329,054 | 7/1994 | Theriot . |

FOREIGN PATENT DOCUMENTS

| | | |
|---|---|---|
| 50-005701 | 1/1975 | Japan . |
| 1025737 | 3/1989 | Japan . |

OTHER PUBLICATIONS

Article entitled *Use of Tetrabromophthalic Anhydride (TBPA) in the Construction of Fire–Retardant Polyester and Epoxy Resins* by Sydney M. Spatz, Herman Stone, Marvin Koral, Russell I. Steiner, and Hervey W. Ackerman, Jr. published in Ind. Eng. Chem. Prod. Res. Devel., vol. 8, No. 4, Dec. 1969.

Article entitled *Discoloration of Tetrabromophthalic Anhydride Polyester Resins* by Sydney M. Spatz, Herman Stone, Marvin Koral, Russell I. Steiner, and Hervey W. Ackerman, Jr. published in Ind. Eng. Chem. Prod. Res. Devel., vol. 8, No. 4, Dec. 1969.

*Primary Examiner*—Paul J. Killos
*Attorney, Agent, or Firm*—Woodard, Emhardt, Naughton, Moriarty & McNett

[57] ABSTRACT

A method of preparing tetrabromobenzoate compounds from tetrabromophthalic anhydride by reacting tetrabromophthalic anhydride with alcohol in the presence of a decarboxylation catalyst. The reaction may be carried out in an excess of alcohol, or with a near stoichiometric amount of alcohol by performing the reaction in an inert solvent.

20 Claims, No Drawings

ONE-POT SYNTHESIS OF RING-BROMINATED BENZOATE COMPOUNDS

FIELD OF THE INVENTION

The present invention relates generally to methods for synthesizing tetrabromobenzoates, and more particularly to a method for their one-pot synthesis in high yield from tetrabromophthalic anhydride.

BACKGROUND OF THE INVENTION

The formation of tetrabromobenzoates has been disclosed by the prior art as being a minor, undesirable by-product in the synthesis of tetrabromophthalates from tetrabromophthalic anhydride. See, e.g., U.S. Pat. Nos. 5,049,697 and 5,208,366, both to Bohen et al; and Spatz et al., 8 Ind. Eng. Chem. Prod. Res. Develop., 391 (1969). In those references, tetrabromobenzoate is formed through decarboxylation of a reaction intermediate, and conditions are stated by which this undesirable side-reaction can be avoided.

The direct synthesis of tetrabromobenzoates has preferably been accomplished in the prior art through esterification of tetrabromobenzoic acid using an expensive metal or organometallic esterification catalyst. See, U.S. Pat. Nos. 5,049,697 and 5,208,366, both to Bohen et at. A disadvantage to this method is that tetrabromobenzoic acid is not readily available, and therefore must be synthesized prior to esterification. The esterification of tetrabromobenzoic acid requires long reaction times (22–70 hours), and requires the use of a metal or organometallic esterification catalyst which necessitates the complicated removal and disposal of the catalyst at the end of the reaction.

A need therefore exists for a simpler, faster and less expensive method of converting tetrabromophthalic anhydride to tetrabromobenzoate in high yield. The present invention addresses that need.

SUMMARY OF THE INVENTION

Briefly describing one aspect of the present invention, there is provided an improved method of preparing tetrabromobenzoate compounds from tetrabromophthalic anhydride. In particular, a one-pot method is disclosed wherein tetrabromobenzoates are prepared by reacting tetrabromophthalic anhydride with the appropriate alcohol in the presence of a decarboxylation catalyst. The reaction proceeds through rapid esterification of the anhydride, followed by decarboxylation to yield the tetrabromobenzoate.

One object of the present invention is to provide a faster, less expensive method of synthesizing tetrabromobenzoates from tetrabromophthalic anhydride.

Further objects and advantages of the invention will be apparent from the following description.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the illustrated embodiments, and such further applications of the principles of the invention as illustrated herein being contemplated as would normally occur to one skilled in the art to which the invention pertains.

As previously indicated, the present invention relates to a method for converting tetrabromophthalic anhydride to a selected tetrabromobenzoate. In general, tetrabromophthalic anhydride is reacted with the appropriate alcohol in the presence of a decarboxylation catalyst. In one preferred embodiment the reaction is performed in an inert solvent to further minimize the creation of phthalates.

The general synthetic process is shown in Scheme I below, wherein the group R generally represents an organic group having for example up to about 30 carbon atoms:

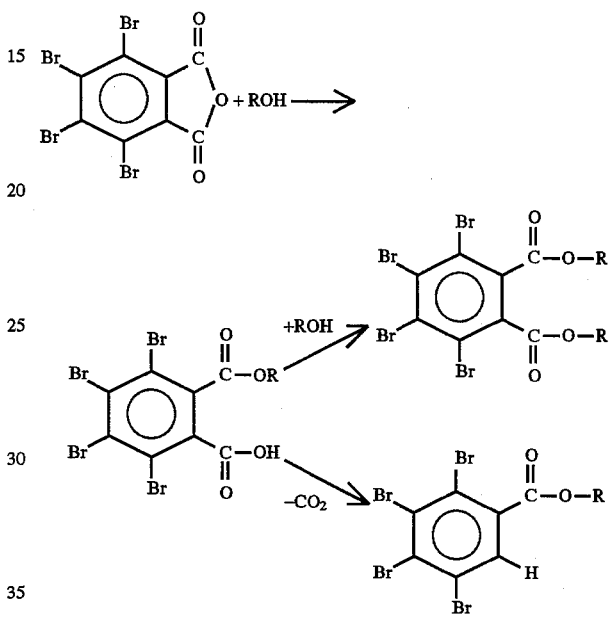

Scheme I

Thus, preferred processes of the invention will form compounds of the formula (I):

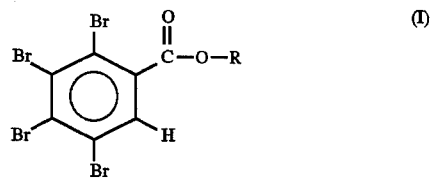

wherein R is an organic group provided by the alcohol used in the reaction, the organic group preferably having up to about 30 carbon atoms, and optionally being substituted with one or more groups such as alkoxy, halo, amino, thio, and the like.

Alcohols useful in the present invention include alcohols having a boiling point of between about 160° C. and about 230° C., preferably between 180° C. and 205° C. These alcohols provide the advantage of allowing the decarboxylation reaction to proceed at a reasonable rate, while still allowing for ease of stripping the excess alcohol from the product at the end of the reaction. Preferably the alcohol is a non-halogenated, non-sulfur-containing, non-nitrogen-containing alcohol. Branched chain alcohols are most preferred.

Appropriate alcohols with boiling points between about 160° C. and about 230° C. include 2-(2-methoxy) ethoxyethanol, 2-butoxyethanol, 3,3-diethoxy-1-propanol, di(propylene glycol) methyl ether, 2-ethyl-1-hexanol, 3-ethyl-1-hexanol, 3,4-dimethyl-1-hexanol, 3,5-dimethyl-1- hexanol, 3-methyl-1-heptanol, 4-methyl-1-heptanol, 2-octanol, 5-methyl-1-heptanol, 3-octanol, 2-propyl-1-pentanol, 2,6-dimethyl-4-heptanol, 2-nonanol, dihydromyrcenol, 3,5,5-trimethyl-1-hexanol, 3,7-dimethyl-1-octanol, 3,7-dimethyl-3-octanol, mixed $C_7$ and $C_9$ alcohols (hereinafter "mixed $C_7/C_9$ alcohols"), isooctyl alcohol, mixed $C_9$ alcohols, 3-furanmethanol, furfuryl alcohol, tetrahydrofurfuryl alcohol, 3-acetyl-1-propanol, 2-isopropoxyethanol, 3-methoxy-1-butanol, 2-cyclohexen-1-ol, 1,5-hexadien-3-ol, t,t-2,4-hexadien-1-ol, 3-hexyn-1-ol, 5-hexyn-1-ol, cyclopentanemethanol, 4-methyl-1-pentanol, 3-(trimethylsilyl)allyl alcohol, benzyl alcohol, 3-trimethylsilyl-1-propanol, 3-cyclohexen-1-methanol, 3-methyl-2-cyclohexen-1-ol, cycloheptanol, cyclohexylmethanol, 1-methylcyclohexanol, 2methylcyclohexanol, 3-methylcyclohexanol, 4-methylcyclohexanol, 1-heptanol, 2-heptanol, propylene glycol butyl ether, 2-methylbenzyl alcohol, 3-methylbenzyl alcohol, 4-methylbenzyl alcohol, phenethyl alcohol, sec-phenethyl alcohol, 1-octyn-3-ol, cycloheptanemethanol, 2-cyclohexylethanol, 1-cyclohexylethanol, cyclooctanol, 3-cyclopentyl-1-propanol, 2,3-dimethylcyclohexanol, 2,6dimethylcyclohexanol, 3,5-dimethylcyclohexanol, 2ethylcyclohexanol, 4-ethylcyclohexanol, 1-octanol, 6-methyl-5-hepten-2-ol, 1-octen-3-ol, 6-methyl-2-heptanol, 2-(cyclohexyloxy)ethanol, 2,2-dimethoxycyclohexanol, 2,4,4-trimethyl-1-pentanol, 1-phenyl-1-propanol, 1-phenyl-2-propanol, 2-phenyl-2-propanol, 3-nonyn-1-ol, 2,4-dimethyl-2,6-heptadien-1-ol, 3-cyclohexyl-1-propanol, 3,5,5-trimethyl-2-cyclohexen-1-ol, 3-nonen-1-ol, 3-ethyl-2,2-dimethyl-3-pentanol, 1-nonanol, 1-myrtenol, 2-phenyl-3-butyn-2-ol, 1-phenyl-1-cyclopropanemethanol, 2-methyl-1-phenyl-2-propanol, isopulegol, linalool, 1-myrtenol, nerol, terpineol, terpinen-4-ol, citronellol, 4-cyclohexyl-1-butanol, 2-decanol, 4-decanol, mixed $C_7$–$C_{11}$ alcohols, isodecyl alcohol, hexyl decyl alcohol, 1,3-dibromo-2-propanol, 2,3-dibromopropanol, 1,3-dichloro-2-propanol, 1,3-difluoro-2-propanol, 3-bromo-1-propanol, 3-chloro-1-propanol, 4-chloro-1-butanol, 2-(methylthio)ethanol, 3-bromo-3-buten-1-ol, 3-pyrrolidinol, 1,4-dibromo-2-butanol, 2-(2-chloroethoxy)ethanol, 3-methylthio-1-propanol, 3-thiophenemethanol, 2,2-bis(chloromethyl)-1-propanol, tetrahydro-4H-pyran-4-ol, 3-bromo-2,2-dimethyl-1-propanol, 2-(3-thienyl)ethanol, 3-chloro-2,2-dimethyl-1-propanol, 1-methyl-3-pyrrolidinol, 4-(methylthio)-1-butanol, 2-(trimethylsilyl)ethanol, 2-(2-thienyl ethonol, tetrahydropyran-2-methanol, 6-bromo-1hexanol, 6-chloro-1-hexanol, 7-bromo-1-heptanol, N,N-diethylethanolamine, 1-methyl-2-pyrrolidinemethanol, 1-piperideneethanol, 3-(methylthio)-1-hexanol, 3-diethylamino-1-propanol, 2-(diisopropylamino)ethanol and 2-{[2-(dimethylamino)ethyl]methylamino}ethanol. Of these, 3-furanmethanol, furfuryl alcohol, tetrahydrofurfuryl alcohol, 3-acetyl-1-propanol, 2-isopropoxyethanol, 3-methoxy-1-butanol, 2-cyclohexen-1-ol, 1,5-hexadien-3-ol, t,t-2,4-hexadien-1-ol, 3-hexyn-1-ol, 5-hexyn-1-ol, cyclopentanemethanol, 4-methyl-1-pentanol, 3-(trimethylsilyl)allyl alcohol, cyclohexylmethanol, 3-trimethylsilyl-1-propanol, benzyl alcohol, 3-cyclohexen-1-methanol, 3-methyl-2-cyclohexen-1-ol, cycloheptanol, 1-methylcyclohexanol, 2-methylcyclohexanol, 3-methylcyclohexanol, 4-methylcyclohexanol, 1-heptanol, 2-heptanol, propylene glycol butyl ether, 2-methylbenzyl alcohol, 3-methylbenzyl alcohol, 4-methylbenzyl alcohol, phenethyl alcohol, sec-phenethyl alcohol, 1-octyn-3-ol, cycloheptanemethanol, 2-cyclohexylethanol, 1-cyclohexylethanol, cyclooctanol, 3-cyclopentyl-1-propanol, 2,3-dimethylcyclohexanol, 2,6-dimethylcyclohexanol, 3,5-dimethylcyclohexanol, 2-ethylcyclohexanol, 4-ethylcyclohexanol, 6-methyl-5-hepten-2-ol, 1-octen-3-ol, 2-(cyclohexyloxy)ethanol, 2,2-dimethoxycyclohexanol, 6-methyl-2-heptanol, 1-octanol, 2,4,4-trimethyl-1-pentanol, 1-phenyl-1-propanol, 1-phenyl-2-propanol, 2-phenyl-2-propanol, 2,4-dimethyl-2,6-heptadien-1-ol, 3-nonyn-1-ol, 3,5,5-trimethyl-2-cyclohexen-1-ol, 3-cyclohexyl-1-propanol, 3-nonen-1-ol, 1-nonanol, 3-ethyl-2,2-dimethyl-3-pentanol, 2-phenyl-3-butyn-2-ol, 1-phenyl-1-cyclopropanemethanol, 1-myrtenol, isopulegol, 2-methyl-1-phenyl-2-propanol, linalool, 1-myrtenol, nerol, terpineol, terpinen-4-ol, citronellol, 2-decanol, 4-decanol, 4-cyclohexyl-1-butanol, mixed $C_7/C_{11}$ alcohols, isodecyl alcohol and hexyl decyl alcohol are preferred, while 3,3-diethoxy-1-propanol, 2-(2-methoxy)ethoxyethanol, 3,4-dimethyl-1-hexanol, 2-butoxyethanol, di(propylene glycol) methyl ether, 3-ethyl-1-hexanol, 2-ethyl-1-hexanol, 3,5-dimethyl-1-hexanol, 3-methyl-1-heptanol, 4-methyl-1-heptanol, 5-methyl-1-heptanol, 2-octanol, 3-octanol, 2-propyl-1-pentanol, 2,6-dimethyl-4-heptanol, 2-nonanol, 3,5,5-trimethyl-1-hexanol, dihydromyrcenol, 3,7-dimethyl-1-octanol, 3,7-dimethyl-3-octanol, mixed $C_7/C_9$ alcohols, isooctyl alcohol and mixed $C_9$ alcohols are most preferred.

Alternatively, alcohols with boiling points below 160° C. can be used in combination with a high boiling solvent. In particular, alcohols with boiling points between about 100° C. and 160° C. may advantageously be used in that manner. Preferred are non-halogenated, non-sulfur-containing, non-nitrogen-containing alcohols with boiling points between about 130° C. and 160° C. Branched chain alcohols are most preferred.

Examples of appropriate alcohols with boiling points lower than about 160° C. include 2-ethoxyethanol, amyl alcohol, 2-methyl-1-butanol, 3-methyl-1-butanol, 3-ethoxy-1-propanol, 2-ethyl-1-butanol, 4-methyl-2-pentanol, 2,4-dimethyl-3-pentanol, acetol, 2-butyne-1-ol, 3-butyn-1-ol, 1-pentyn-3-ol, 2-pentyn-1-ol, 3-pentyn-1-ol, 4-pentyn-1-ol, 4-pentyn-2-ol, cyclobutanemethanol, 3-methyl-2-buten-1-ol, 3-methyl-3-buten-1-ol, 2-penten-1-ol, 4-penten-1-ol, 1-pentanol, cyclohexanol, 1-hexen-3-ol, 2-hexen-1-ol, 3-hexen-1-ol, 4-hexen-1-ol, 5-hexen-1-ol, 1-methylcyclopentanol, 2-methylcyclopentanol, 3-methylcyclopentanol, 4-methyl-3-penten-1-ol, 3,3-dimethyl-1-butanol, 1-hexanol, 2-hexanol, 3-hexanol, 2-methyl-1-pentanol, 3-methyl-1-pentanol, 3-methyl-2-pentanol, t-butyldimethylsilanol, 1-ethynylcyclopentanol, 1,6-heptadien-4-ol, 2,2-dimethyl-3-pentanol, 2,3-dimethyl-3-pentanol, 4,4-dimethyl-2-pentanol, 3-ethyl-3-pentanol, 2-methyl-2-hexanol, 2-methyl-3-hexanol, 5-methyl-2-hexanol, 3,5-dimethyl-1-hexyn-3-ol, 2-chloroethanol, 2,2,3,3-tetrafluoro-1-propanol, propargyl alcohol, 2-chloro-2-propene-1-ol, 1-bromo-2-propanol, 1-chloro-2-propanol, 2-methoxyethanol, 2-(methylsulfonyl)ethanol, 3-butyn-1-ol, 3-buten-1-ol, crotyl alcohol, cyclobutanol, cyclopropanemethanol, 2-methyl-2-propen-1-ol, 1-chloro-2-methyl-2-propanol, 1-butanol, 2-butanol, 2-methyl-1-propanol, 1-methoxy-2-propanol, N,N-dimethylethanolamine, (trimethylsilyl)methanol, 2-methyl-3-butyn-2-ol, 1,4-pentadien-3-ol, 2-methyl-3-buten-1-ol, a-methylcyclopropanemethanol, 1-methylcyclopropanemethanol, 1-penten-3-ol, 3-penten-2-ol, 4-penten-2-ol, t-amyl alcohol, 3-methyl-2-butanol, neopentylalcohol, 2-pentanol, 3-pentanol, 1-(trimethylsilyl)ethanol, 3-methyl-1-pentyn-3-ol, 3-methyl-1-penten-3-ol, 2,3-dimethyl-2-butanol, 3,3-dimethyl-2-butanol, 2-methyl-2-pentanol, 2-methyl-3-pentanol, 3-methyl-3-pentanol, 1-methyl-2-piperidinemethanol, 1-methyl-3-piperidinemethanol, and 1-diethylamino-2-propanol. Of these, acetol, 2-butyne-1-ol, 3-butyn-1-ol, 1-pentyn-3-ol, 2-pentyn-1-ol, 3-pentyn-1-ol, 4-pentyn-1-ol, 4-pentyn-2-ol, cyclobutanemethanol, 3-methyl-2-buten-1-ol, 3-methyl-3-buten-1-ol, 2-penten-1-ol, 4-penten-1-ol, 1-pentanol, cyclohexanol, 1-hexen-3-ol, 2-hexen-1-ol, 3-hexen-1-ol, 4-hexen-1-ol, 5-hexen-1-ol, 1-methylcyclopentanol, 2-methylcyclopentanol, 3-methylcyclopentanol, 4-methyl-3-penten-1-ol, 3,3-dimethyl-1-butanol, 1-hexanol, 2-hexanol, 3-hexanol, 2-methyl-1-pentanol, 3-methyl-1-pentanol, 3-methyl-2-pentanol, t-butyldimethylsilanol, 1-ethynylcyclopentanol, 1,6-heptadien-4-ol, 2,2-dimethyl-3-pentanol, 2,3-dimethyl-3-pentanol, 4,4-dimethyl-2-pentanol, 3-ethyl-3-pentanol, 2-methyl-2-hexanol, 2-methyl-3-hexanol, 5-methyl-2-hexanol and 3,5-dimethyl-1-hexyn-3-ol are preferred, while 2-ethoxyethanol, amyl alcohol, 2-methyl-1-butanol, 3-methyl-1-butanol, 3-ethoxy-1-propanol, 2-ethyl-1-butanol, 4-methyl-2-pentanol and 2,4-dimethyl-3-pentanol are most preferred.

Surprisingly, increased selectivity towards the benzoate has been observed when certain alcohols are used. For example, 2-butoxyethanol or 2-methoxyethoxyethanol show high selectivity towards the benzoate, and are particularly preferred for use in the invention for that reason.

It has also been discovered that the selection of the alcohol affects the color of the product formed, with some alcohols yielding a lighter colored product than others. In general, a lighter colored product is desired. A desired shade of product may therefore be obtained by selecting an appropriate alcohol to use in the synthetic process of the present invention.

The decarboxylation reaction can be carried out using any appropriate catalyst that favors decarboxylation over esterification, for example providing in the reaction at hand a reaction product at least 50% by weight comprised of the desired ring-brominated benzoate compound. Preferred catalysts include alkali carbonates, alkali bicarbonates and caustic alkalis. Sodium and potassium carbonate and bicarbonate, lithium carbonate and sodium aluminate are particularly preferred due to their relatively low cost and ready availability.

The catalyst loading effects the product ratio of tetrabromobenzoate to tetrabromophthalate ester. With a lower catalyst loading, the decarboxylation step is slower, which allows greater formation of diester. With a higher catalyst loading, lower amounts of diester are formed but increasing amounts of other by-products have been observed. The desired catalyst loading is between 1 and 25 mole percent, and preferable between 5 and 15%, based upon the tetrabromophthalic anhydride charge. Some catalysts yield a lighter colored product.

As indicated above, the reaction may be accomplished in an excess of alcohol (e.g., 3 to 6 mole equivalents based on the tetrabromophthalic anhydride used), although an inert solvent may alternatively be used. When the reaction is carried out in an excess of alcohol, a significant amount of the corresponding tetrabromophthalate ester is also formed.

In one preferred aspect of the invention the reaction is carried out in an inert solvent, such as a high boiling ether, with near stoichiometric amounts of the alcohol (e.g., 1.0 to 1.25 mole equivalents). Inert solvents particularly preferred for the invention have a boiling point of between about 160° C. and about 230° C., and are preferably from the family of ethers such as, for example, 2-ethoxyethylether. The inert solvent should have solubility properties which allow the reaction to proceed at a reasonable rate, particularly by accommodating the solubility of the polar intermediate (or its salt complex).

By this invention, a low viscosity liquid product can be obtained which contains 50–90% tetrabromobenzoate and 1–40% of the corresponding phthalate. In one aspect of the invention the one-pot process provides at least about 60% tetrabromobenzoate, while other preferred aspects provide at least about 70% tetrabromobenzoate. Further preferred embodiments provide at least about 80% tetrabromobenzoate, with one aspect of the invention providing at least about 85% tetrabromobenzoate.

The total organic bromine content of the product, which is an important factor for efficiency as a flame retardant, can be adjusted by the alcohol and/or solvent used in the synthesis and/or the catalyst loading, but generally falls within the range of 50–70%.

It is to be appreciated that when an excess of alcohol is used the reaction favors the formation of phthalates, whereas when near stoichiometric amounts of alcohol are used the reaction favors the formation of benzoate. Accordingly, in one aspect of the invention a near stoichiometric amount of alcohol is reacted with tetrabromophthalic anhydride inert solvent to produce product comprising at least about 85% tetrabromobenzoate compound.

The ring-brominated benzoates produced in accordance with the invention are useful as flame retardants in a variety of polymer resin systems. For example, the bromobenzoate compound can be incorporated into thermoset polymers such as polyurethanes by including the bromobenzoate in the polyurethane mixture as the polymer is prepared. This process has been referred to as the "one-shot" technique, and is described with more particularity in common reference materials such as the Modern Plastics Encyclopedia, Vol. 71, No. 12 (1994), and was used in Examples 11 through 15 below.

The incorporation of bromobenzoates into polyvinyl chlorides may be accomplished either by including the desired tetrabromobenzoate in the mixture as the polyvinyl chloride is being formed, or by incorporating the bromobenzoate into polymerized polyvinyl chloride. Specific techniques for incorporating additives such as bromobenzoates into thermoplastics such as PVC are known to the art and may be used to accomplish that step.

As will be understood, the level of bromobenzoate incorporated into the polymer resin to provide an effective flame retarding amount will vary widely in accordance with many factors such as the particular resin used, the application contemplated, other additives present, etc. Typically, the bromobenzoate will be incorporated at levels between about 2% and 50% of the total system weight, and more commonly at levels between about 5% and 30% of the total system weight.

It will be understood that other conventional additives may also be incorporated into the polymer systems. For example, the bromobenzoate product can be incorporated along with other brominated flame retardant compounds; however, it is preferred in this regard that the bromobenzoate compound constitute a predominant portion (i.e. greater than 50% by weight) of the total amount of brominated flame retardant included in the system. Flame retardant materials such as oxides of Group V elements, especially antimony oxides, and/or phosphorous-containing compounds, can also be included. Additional conventional additives may include antioxidants, antistatic agents, colorants, fibrous reinforcements, fillers, foaming/blowing agents, catalysts, heat stabilizers, impact modifiers, lubricants, plasticizers, processing aids, UV light stabilizers, crosslinking/curing agents, etc.

Reference will now be made to specific examples using the processes described above. It is to be understood that the examples are provided to more completely describe preferred embodiments, and that no limitation to the scope of the invention is intended thereby. All percentages given in these Examples and throughout this document are given in weight %, unless specified otherwise.

EXAMPLE 1

Synthesis of 2-ethylhexyltetrabromobenzoate from tetrabromophthalic anhydride in 2-ethylhexanol solvent using sodium bicarbonate catalyst Tetrabromophthalic anhydride (232g, 0.50 moles), 2-ethylhexanol (196 g, 1.5 moles), and sodium bicarbonate (3.8 g, 0.045 moles) were charged to a stirred, glass vessel. The mixture was heated to reflux, with the water of reaction being collected in a Dean-Stark trap. After $CO_2$ evolution ceased (approx. 3.5 hours), the reaction was cooled and filtered to remove the catalyst. The excess 2-ethylhexanol was stripped off under vacuum yielding a clear, amber liquid product. GLC assay indicated 76.1% tetrabromobenzoate and 13.0% tetrabromophthalic diester; organic bromide ("OBr") of 55.16%; TGA 5% wt. loss 217° C.; Gardner color 11.

EXAMPLE 2

Synthesis of 2-ethylhexyltetrabromobenzoate from tetrabromophthalic anhydride in 2-ethylhexanol solvent using potassium bicarbonate catalyst Tetrabromophthalic anhydride (232 g, 0.50 moles), 2-ethylhexanol (196 g, 1.5 moles), and potassium bicarbonate (5.5 g, 0.055 moles) were charged to a stirred, glass vessel. The mixture was heated to reflux, with the water of reaction being collected in a Dean-Stark trap. After $CO_2$ evolution ceased (approx. 3.5 hours), the reaction was cooled and filtered to remove the catalyst. The excess 2-ethylhexanol was stripped off under vacuum yielding a clear, amber liquid product. GLC assay 66.7% tetrabromobenzoate, 15.8% tetrabromophthalic diester; OBr 54.04%; TGA 5% wt. loss 221° C.; Gardner color 12.

EXAMPLE 3

Synthesis of 2-ethylhexyltetrabromobenzoate from tetrabromophthalic anhydride in 2-ethylhexanol solvent using potassium carbonate catalyst Tetrabromophthalic anhydride (464 g, 1.0 moles), 2-ethylhexanol (391 g, 3.0 moles), and potassium carbonate (15.1 g, 0.11 moles) were charged to a stirred, glass vessel. The mixture was heated to reflux, with the water of reaction being collected in a Dean-Stark trap. After $CO_2$ evolution ceased (approx. 3.5 hours), the reaction was cooled and filtered to remove the catalyst. The excess 2-ethylhexanol was stripped off under vacuum yielding a clear, amber liquid product. GLC assay 63.5% tetrabromobenzoate, 11.5% tetrabromophthalic diester; OBr 52.29%; THA 5% wt. loss 235° C.; Gardner color 14.

EXAMPLE 4

Synthesis of 2-ethylhexyltetrabromobenzoate from tetrabromophthalic anhydride in 2-ethylhexanol solvent using lithium carbonate catalyst Tetrabromophthalic anhydride (464 g, 1.0 moles), 2-ethylhexanol (390 g, 3.0 moles), and lithium carbonate (8.1 g, 0.11 moles) were charged to a stirred, glass vessel. The mixture was heated to reflux, with the water of reaction being collected in a Dean-Stark trap. After $CO_2$ evolution ceased (approximately 8.0 hours), the reaction was cooled and filtered to remove the catalyst. The excess 2-ethylhexanol was stripped off under vacuum yielding a clear, amber liquid product. GLC assay 60.7% tetrabromobenzoate, 10.4% tetrabromophthalic diester; OBr 51.9%; TGA 5% wt. loss 240° C.

EXAMPLE 5

Synthesis of 2-ethylhexyltetrabromobenzoate from tetrabromophthalic anhydride in 2-ethoxyethylether solvent Tetrabromophthalic anhydride (1391 g., 3.00 moles), 2ethylhexanol (469 g, 3.60 moles), 2-ethoxyethylether (771 g, 4.75 moles), and sodium bicarbonate (25 g, 0.30 moles) were charged to a stirred, glass vessel. The mixture was brought to reflux, with the water of reaction being collected in a Dean-Stark trap. After $CO_2$ evolution had ceased (approximately 3 hours), the reaction was cooled and filtered to remove the catalyst. The 2-ethoxyethylether and excess 2-ethylhexanol were stripped off under vacuum yielding a clear, amber liquid product. GLC assay 85.0% tetrabromobenzoate, 1.6% tetrabromophthalic diester; OBr 56.99%; TGA 5% wt. loss 209° C., Gardner color 11.

EXAMPLE 6

Synthesis of 2-butoxyethyltetrabromobenzoate

Tetrabromophthalic anhydride (232 g, 0.5 moles), 2-butoxyethanol (226 g, 1.9 moles), and potassium bicarbonate (8.3 g, 0.083 moles) were charged to a stirred, glass vessel. The mixture was heated to reflux, with the water of reaction being collected in a Dean-Stark trap. After $CO_2$ evolution had ceased (approximately 3 hours), the reaction was cooled and filtered to remove the catalyst. Excess 2-butoxyethanol was stripped off under vacuum yielding a clear, amber product. GLC assay 82.4% tetrabromobenzoate, 7.9% tetrabromophthalic diester; OBr 57.84%; TGA 5% wt. loss 225° C.; Gardner color 13.

EXAMPLE 7

Synthesis of 2-methoxyethoxyethyltetrabromobenzoate

Tetrabromophthalic anhydride (232 g, 0.5 moles), 2-methoxyethoxyethanol (238 g, 2.0 moles), and potassium bicarbonate (8.3 g, 0.083 moles) were charged to a stirred, glass vessel. The mixture was heated to reflux, with the water of reaction being collected in a Dean-Stark trap. After $CO_2$ evolution had ceased (approximately 2 hours), the reaction was cooled and filtered to remove the catalyst. Excess 2-methoxyethoxyethanol was stripped off under vacuum yielding a clear, amber product. GLC assay 81.2% tetrabromobenzoate, 0.4% tetrabromophthalic diester; OBr 59.82%; TGA 5% wt. loss 180° C.; Gardner color 14.

EXAMPLE 8

Synthesis of a tetrabromobenzoate from mixed $C_7/C_9$ alcohols

Tetrabromophthalic anhydride (464 g, 1.0 moles), BASF $C_7/C_9$ alcohol (500 mls), and sodium bicarbonate (8.4 g, 0.10 moles) were charged to a stirred, glass vessel. The mixture was heated to reflux, with the water of reaction being collected in Dean-Stark trap. After $CO_2$ evolution had ceased (approximately 3.5 hours), the reaction was cooled and filtered to remove the catalyst. Excess alcohol was stripped off under vacuum yielding a clear, golden colored product. OBr 52.77%; TGA 5% wt. loss 231° C.; Gardner color 5.

EXAMPLE 9

Use of a tetrabromobenzoate in flexible polyurethane foam

The 2-ethylhexyltetrabromobenzoate prepared in Example 1 was added to flexible polyurethane foam prepared by the formulation below. All components are expressed in parts by weight.

| Component | Parts by Weight |
| --- | --- |
| 3,000 molecular weight glycerine based heteropolyol | 100 |
| 2-ethylhexyltetrabromobenzoate of Example 1 | 18 |
| Water | 4.5 |
| Amine catalyst (triethylene diamine/dimethyl-aminoethyl ether) | 0.33 |
| L-620 silicone surfactant* | 0.9 |
| Stannous octoate | 0.25 |
| Toluene diisocyanate (80/20) | 51.2 |

*product of OSI Specialties

Lab preparation yielded a flexible polyurethane foam with a density of 1.5 lb/ft$^2$ and an airflow of 4.0. The foam met the criteria of the California Bulletin 117 combustibility test part A with an average burn distance of 2.5 inches and no burn time. It also met the criteria of part D with a weight retention in the smolder test in excess of 98%.

EXAMPLE

Use of tetrabromobenzoate in reaction injection molded polyurethane

A commercial flame retardant reaction injection molded (RIM) polyurethane system was used for evaluation of the 2-ethylhexyltetrabromobenzoate of Example 1. The standard RIM system contains 15% of a blend of pentabromo-diphenyl oxide and an aromatic phosphate ester (DE-60FS) as a combustibility modifier. RIM parts were molded containing this standard combustion modifier and containing the same level (15%) of a 2:1 blend of 2-ethylhexyltetrabromobenzoate and triethyl phosphate (BB/TEP). Results are tabulated below.

| Combustion Modifer | UL-94 Rating | Heat Distortion Temperature |
| --- | --- | --- |
| 15% DE60FS | V-0 | 59° C. |
| 15% BB/TEP | V-0 | 62° C. |

Both combustion modifiers allowed the polymer system to meet the desired combustibility standard, UL-94 V-0, but the blend containing the tetrabromobenzoate maintained the key physical property, heat distortion, better than the standard combustibility modifier.

EXAMPLE 11

Use of 2-Ethylhexyltetrabromobenzoate in rigid polyurethane foam

The 2-ethylhexyltetrabromobenzoate of Example 1 was added to a rigid polyurethane foam as indicated in the formulation below. The resultant foam, which had good cell structure and a density of 2.1 lbs. per cubic foot, was tested for combustibility in a four foot tunnel designed to correlate with the results obtained on a larger scale in the 25 foot tunnel test (ASTM E-84). The four foot tunnel test consists of a Fisher burner with a 1950° F. butane flame placed under a 4 foot long specimen inclined at an angle of fifteen degrees. Smoke is measured by passing combustion products between a light beam and photocell. Standards with known 25 foot tunnel test values are used for calibration.

| Component | Parts by Weight |
| --- | --- |
| Sucrose polyol (N500 OH#) | 34 |
| Tetrabromophthalate Diol (N215 OH#) | 51 |
| 2-ethylhexyltetrabromobenzoate of Example 1 | 15 |
| L-5440 surfactant (product of OSI Spec) | 1.5 |
| Dimethylcyclohexylamine | 0.8 |
| Dichlorofluoroethane | 24.7 |
| Polymeric MDI (N125 index) | 80.6 |

Combustibility results of four foot tunnel testing of this foam were a predicted flame spread of 19 and smoke evolution of 170. Both are well within the requirements for Class 1 of less than 25 flame spread and 450 smoke for the 25 foot tunnel. Although tetrabromophthalate diol contributes to the combustibility test performance, over 60 parts of this diol are needed in this formulation when the tetrabromobenzoate is not present to attain less than 25 flame spread in the four foot tunnel test.

EXAMPLE 12

Use of 2-Ethylhexyltetrabromobenzoate in unsaturated polyester resin

To an orthophthalic/propylene glycol based resin containing 35% styrene was added 14.5 parts per hundred resin (phr) 2-ethylhexyltetrabromophthalate of Example 2 and 2 phr antimony oxide. An eighth inch thick, 25% glass laminate was prepared using 1.5 oz/yd$^2$ glass mat. This laminate had a V-0 rating when tested by the UL-94 combustibility test.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

We claim:

1. A method for preparing tetrabromobenzoate compounds from tetrabromophthalic anhydride, comprising reacting tetrabromophthalic anhydride with an alcohol in the presence of a catalyst that favors decarboxylation over esterification.

2. A method according to claim 1 wherein said alcohol has a boiling point of between 160° C. and 230° C.

3. A method according to claim 1 wherein said alcohol has a boiling point of between 180° C. and 205° C.

4. A method according to claim 1 wherein said alcohol is a member of the selected group consisting of 2-(2-methoxy) ethoxyethanol, 2-butoxyethanol, 3,3-diethoxy-1-propanol, di(propylene glycol) methyl ether, propylene glycol butyl ether 2-ethyl-1-hexanol, 3-ethyl-1-hexanol, 3,4-dimethyl-1-hexanol, 3,5-dimethyl-1-hexanol, 3-methyl-1-heptanol, 4-methyl-1-heptanol, 5-methyl-1-heptanol, 2-octanol, 3-octanol, 2-propyl-1-pentanol, 2,6-dimethyl-4-heptanol, 2-nonanol, 3,5,5-trimethyl-1-hexanol, dihydromyrcenol, 3,7-dimethyl-1-octanol, 3,7-dimethyl-3-octanol, mixed $C_7/C_9$ alcohols, isooctyl alcohol and mixed $C_9$ alcohols.

5. A method according to claim 1 wherein said alcohol is a member selected from the group consisting of 2-(2-methoxy)ethoxyethanol and 2-butoxyethanol.

6. A method according to claim 1 wherein said alcohol is a member selected from the group consisting of 2-ethyl-1-hexanol, isooctyl alcohol, mixed $C_7/C_9$ alcohols and mixed $C_9$ alcohols.

7. A method according to claim 1 wherein said reacting of tetrabromophthalic anhydride with alcohol takes place in an inert solvent.

8. A method according to claim 7 wherein said alcohol is present in near stoichiometric amount.

9. A method according to claim 7 wherein said inert solvent has a boiling point of between about 160° C. and 230° C.

10. A method according to claim 7 wherein said inert solvent has a boiling point of between about 180° C. and 205° C.

11. A method according to claim 7 wherein said inert solvent is selected from the family of high boiling ethers.

12. A method according to claim 7 wherein said inert solvent is 2-ethoxyethylether.

13. A method according to claim 7 wherein said alcohol has a boiling point of between about 100° C. and 160° C.

14. A method according to claim 7 wherein said alcohol has a boiling point of between about 130° C. and 160° C.

15. A method according to claim 7 wherein said alcohol is a member selected from the group consisting of 2-ethoxyethanol, amyl alcohol, 2-methyl-1-butanol, 3-methyl-1-butanol, 3-ethoxy-1-propanol, 2-ethyl-1-butanol, 4-methyl-2-pentanol, 2,4-dimethyl-3-pentanol, propylene glycol propyl ether, and propylene glycol t-butyl ether.

16. A method for preparing tetrabromobenzoate compounds from tetrabromophthalic anhydride, comprising reacting tetrabromophthalic anhydride with an alcohol in the presence of a catalyst that favors decarboxylation over esterification; wherein said catalyst is an alkali carbonate or bicarbonate, or a caustic alkali.

17. A method according to claim 16 wherein said catalyst is a member selected from the group consisting of sodium carbonate, sodium bicarbonate, potassium carbonate, potassium bicarbonate, lithium carbonate and sodium aluminate.

18. A method according to claim 1 wherein the product contains at least 50% tetrabromobenzoate.

19. A method according to claim 1 wherein the product contains 50–90% tetrabromobenzoate and 1–40% tetrabromophthalate.

20. A method for preparing a composition predominantly comprised of tetrabromobenzoate, comprising:

reacting an amount of an alcohol or a mixture of alcohols of the formula R—OH wherein R is an organic group having up to about 30 carbon atoms, with an amount of tetrabromophthalic anhydride in the presence of a catalyst so as to form a reaction product at least 50% by weight comprised of one or more tetrabromobenzoate compounds of the formula:

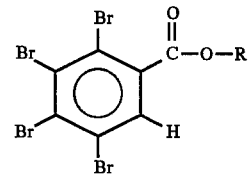

wherein R is as defined above.

* * * * *

UNITED STATES PATENT AND TRADEMARK OFFICE
CERTIFICATE OF CORRECTION

PATENT NO. : 5,637,757
DATED : June 10, 1997
INVENTOR(S) : John E. Hill et al.

It is certified that error appears in the above-identified patent and that said Letters Patent is hereby corrected as shown below:

In col. 3, line 16, please insert a hyphen "-" after "2".

In col. 3, line 23, please insert a hyphen "-" after "6".

In col. 3, line 24, please insert a hyphen "-" after "2".

In col. 3, line 47, please insert a hyphen "-" after "1".

In col. 6, line 21, please insert --in an-- before "inert".

In col. 8, line 17, please insert a hyphen "-" after "2", first occurrence.

In col. 9, line 36, please insert --10-- after "EXAMPLE".

Signed and Sealed this

Eighteenth Day of November 1997

Attest:

BRUCE LEHMAN

Attesting Officer

Commissioner of Patents and Trademarks